United States Patent [19]

Sheldon et al.

[11] 4,036,887

[45] July 19, 1977

[54] PREPARATION OF 3-BROMOBENZALDEHYDE

[75] Inventors: Roger A. Sheldon; Johannes W. van der Meer; Pieter A. Verbrugge; Albertus J. Mulder, all of Amsterdam, Netherlands

[73] Assignee: Shell Oil Company, Houston, Tex.

[21] Appl. No.: 689,758

[22] Filed: May 25, 1976

[30] Foreign Application Priority Data

June 2, 1975 United Kingdom ............... 23771/75

[51] Int. Cl.² .......................................... C07C 47/55
[52] U.S. Cl. ................................................ 260/599
[58] Field of Search ...................................... 260/599

[56] References Cited

U.S. PATENT DOCUMENTS 2,607,802   8/1952   Britton et al. .................... 260/544

OTHER PUBLICATIONS

N. D. Zelinskii Institute of Organic Chemistry, Academy of Sciences USSR, Translated from Izvestiya Nauk SSSR, No. 7, p. 1627, July 1967.
Mills et al., Industrial & Engineering Chemistry, vol. 12, (1973), pp. 160–165.
Eizember et al., Organic Preparations & Procedures Int., vol. 6, (1974), pp. 251-253.
Pearson et al., Jour. Org. Chemistry, (1959), pp. 1412-1419.

Primary Examiner—Bernard Helfin

[57] ABSTRACT

3-Bromobenzaldehyde is prepared by treating benzaldehyde with bromine chloride in the presence of aluminum chloride and a solvent, under specified conditions.

2 Claims, No Drawings

PREPARATION OF 3-BROMOBENZALDEHYDE

BACKGROUND TO THE INVENTION 3-bromobenzaldehyde is of interest as a precursor for preparing insecticidal compounds, so that it is desirable that there be available a process for preparing it efficiently.

DESCRIPTION OF THE INVENTION

It has been found that 3-bromobenzaldehyde can be prepared efficiently by treating benzaldehyde with bromine chloride, in the presence of aluminum chloride, and a polar lower chloroalkane as solvent, under particular conditions, hereinafter described. This process is characterized by minimal consumption of bromine and excellent conversion of the aldehyde precursor in excellent yield of the bromoaldehyde product.

The treatment is suitably conducted by mixing the benzaldehyde with the aluminum chloride in the solvent to form a solution of the complex which benzaldehyde forms with aluminum chloride. To this solution — which may contain some suspended solid complex and/or uncomplexed aluminum chloride — a solution of bromine chloride in the solvent is added. After the reaction is complete, water is added and the resultant mixture is separated into an aqueous phase and an organic phase which is washed with water, dried, concentrated and distilled to give the 3-bromobenzaldehyde product.

The conditions under which the treatment is conducted are:

1. The treatment is conducted at a temperature not exceeding 100° C, and preferably within the range of from about 10° to about 50° C, room temperature ordinarily being suitable and most convenient, operationally.

2. The molar ratio of aluminum chloride to benzaldehyde is maintained within the range of 1.1/1 to 1.5/1, preferably within the range of 1.20/1 to 1.35/1.

3. The molar ratio of benzaldehyde to bromine chloride is maintained within the range of 1/1 to 1/1.5, preferably within the range of 1/1 to 1/1.1/. An excess of bromine chloride — even a local excess — is to be avoided, since the excess will tend to cause poly-bromination. Further, in work-up of the reaction mixture, when water is added, excess bromine chloride may tend to oxidize the aldehyde to the acid. Local excesses can be avoided by slow addition of the bromine chloride to the thoroughly stirred reaction mixture. Use of a solution of the bromine chloride, rather than neat bromine chloride, tends to reduce the possibility of polybromination.

4. The solvent preferably is a polar polychloroalkane such as 1,2-dichloroethane, dichloromethane or chloroform.

5. The benzaldehyde is dissolved in the solvent also containing the aluminum chloride. The amount of the solvent preferably is such that the mixture is saturated with the complex that forms between the benzaldehyde and the aluminum chloride, although the presence of some undissolved solid complex (for example, up to about 25 percent of the complex) will not interfere with the desired treatment. Solid undissolved uncomplexed aluminum chloride also may be present without presenting any problem. The amount of solvent conveniently may be related to the amount of benzaldehyde used. Suitably, the solvent/benzaldehyde ratio, liters per mole, is within the range of from about 1/7 to about ½, preferably within the range of from about 1/6 about ⅓.

6. As indicated in 3., above, to minimize the possibility of undesirable side reactions, it is desirable that the bromine chloride be added slowly, at a controlled rate, to the thoroughly mixed reaction mixture. To moderate the reaction, it is desirable that the bromine chloride be dissolved in a solvent. To simplify conduct of the treatment it is desirable that the solvent the same solvent in which the benzaldehyde and aluminum chloride are dissolved. The amount of solvent used to dissolve the bromine chloride is not known to be critical — it should be sufficient to hold all of the bromine chloride in a fluid solution. More than that minimum may be used, to moderate the reaction with the benzaldehyde. A concentration of about 10 moles of bromine chloride per liter of solvent will be found to be satisfactory.

7. Again, to avoid the possibility of undesirable side reactions, it is essential that the reaction mixture be maintained essentially free from water and from molecular oxygen.

8. Since bromine chloride can react with the chloroalkane solvent, it is desirable to use a freshly prepared solution and/or keep that solution in the dark and/or add a radical scavenger thereto.

By-product hydrogen chloride preferably is removed from the reaction zone essentially as quickly as it is formed, to avoid possible adverse effects from its presence.

Conduct of the process of the invention in specific instances in desirable in the following examples.

EXAMPLE 1

A 500 ml water-cooled glass vessel was fitted with a reflux condenser cooled with a mixture of acetone and solid carbon dioxide, an inlet and an outlet for nitrogen, a propeller stirrer, baffles and a dropping funnel. 200 ml of 1,2-dichloroethane and 1.3 moles of aluminum chloride were placed in the vessel. Then, 1 mole of benzaldehyde was added slowly from the dropping funnel with stirring. The benzaldehyde formed a complex with aluminum chloride, which complex partly dissolved in the 1,2-dichloroethane.

In another vessel 0.5 mole of bromine was added to 20 ml of 1,2-dichloroethane, the vessel being cooled in a mixture of acetone and solid carbon dioxide. 0.5 mole of chlorine was added to the mixture thus formed and subsequently so much 1,2-dichloroethane was added until the total volume was 100 ml.

The solution of bromine chlorine thus obtained was added over a period of 2 hours and 20 minutes through the dropping funnel to the mixture containing the complex of benzaldehyde and aluminum chloride and the reaction mixture was stirred for a further hour. During the reaction hydrogen chloride escaped from the reflux condenser. The temperature of the reaction mixture was kept between 23° and 25° C. Then stirring was discontinued and the reaction mixture was analyzed by means of gas-liquid chromatography. The conversion of the benzaldehyde was 89% and the selectivity to 3-bromobenzaldehyde was higher than 99%.

So much water was mixed with the reaction mixture that the precipitated aluminum hydroxide dissolved. The mixture thus obtained settled into an aqueous layer and an organic layer. The organic layer was separated, washed with 100 ml of water and dried over anhydrous magnesium sulphate. The dried organic layer was boiled down and the residue obtained was separated by distillation into benzaldehyde and a residue of 3-bromobenzaldehyde, boiling at a temperature of 80° C at a pressure of 1.5 Torr.

EXAMPLE 2

The experiment described in Example 1 was repeated with 1.1 moles of aluminum chloride instead of 1.3 moles. Bromination of benzaldehyde to 3-bromobenzaldehyde did occur, but less than 2% of it was converted after 1 hour and less than 5% after 4 hours reaction time.

EXAMPLE 3

The experiment described in Example 1 was repeated with 1.2 moles of aluminum chloride instead of 1.3 moles. After 4 hours reaction time about 70% of the benzaldehyde was converted into 3-bromobenzaldehyde.

We claim:

1. A process for preparing 3-bromobenzaldehyde, which comprises treating, under essentially anhydrous and molecular oxygen-free conditions at a temperature below 100° C, a mixture of benzaldehyde and aluminum chloride, said mixture being at least partially in solution in a lower polar chloroalkane, with a solution of bromine chloride in said chloroalkane, slowly, at a controlled rate, the mole ratio of aluminum chloride-to-benzaldehyde being within the range of from 1.2/1 to 1.5/1 and the molar ratio of benzaldehyde-to-bromine chloride being from 1/1 to 1/1.5.

2. A process according to claim 1 wherein the treatment is conducted at a temperature of from 10° to 50° C, the molar ratio of aluminum chloride to benzaldehyde is within the range of from 1.20/1 to 1.35/1, the molar ratio of benzaldehyde to bromine chloride is within the range of from 1/1 to 1/1.1 and the ratio of solvent to benzaldehyde, liters per mole, is within the range of from about 1/6 to about 1/3.

* * * * *